(12) United States Patent
Zurakowski

(10) Patent No.: US 6,796,311 B1
(45) Date of Patent: Sep. 28, 2004

(54) INCREASED SENSITIVITY CONDOM FOR SIMULTANEOUSLY REDUCING THE TRANSMISSION OF SEXUALLY TRANSMITTED DISEASES

(76) Inventor: Arkadiusz Zurakowski, 2562 Goldkey Estates, Milford, PA (US) 18337

( * ) Notice: Subject to any disclaimer, the term of this patent is extended or adjusted under 35 U.S.C. 154(b) by 54 days.

(21) Appl. No.: 10/409,395

(22) Filed: Apr. 8, 2003

Related U.S. Application Data

(60) Provisional application No. 60/407,728, filed on Sep. 3, 2002.

(51) Int. Cl.[7] .................................................. A61F 6/04
(52) U.S. Cl. ......................... 128/844; 128/842; 128/918
(58) Field of Search ............................... 128/842, 844; 128/918; 604/347–353

(56) References Cited

U.S. PATENT DOCUMENTS

| | | | |
|---|---|---|---|
| 4,281,648 A | 8/1981 | Rogers | |
| 4,432,357 A | 2/1984 | Pomeranz | |
| 5,024,852 A | * 6/1991 | Busnel | ............................ 427/2 |
| 5,284,159 A | * 2/1994 | Wilk | ........................... 128/844 |
| 5,331,974 A | 7/1994 | Sook | |
| 5,377,692 A | 1/1995 | Pfeil | |
| 5,622,186 A | 4/1997 | Schwartz | |
| 5,623,945 A | 4/1997 | Shecterle et al. | |
| 5,823,939 A | * 10/1998 | Tsagarakis | .................... 600/38 |
| 6,098,626 A | * 8/2000 | Kim | ........................... 128/844 |
| 6,651,668 B1 | * 11/2003 | Praml | ........................ 128/844 |

\* cited by examiner

*Primary Examiner*—Michael A. Brown
(74) *Attorney, Agent, or Firm*—Richard L. Miller

(57) ABSTRACT

An increased sensitivity condom for reducing the transmission of diseases. A penis-facing inner sheath extends in a vagina-facing outer sheath, and together therewith, cooperate with a ring. The penis-facing inner sheath is attached to the vagina-facing outer sheath by a web that has apertures therein extending between the penis-facing inner sheath and the vagina-facing outer sheath. The ring is a pump that upon a thrust compresses and draws air in from the ambient through a first check valve in a male-facing side of the ring, out a second check valve in a female-facing side of the ring, and through the apertures in the web to inflate the increased sensitivity condom, while the relief valve prevents rupturing of the increased sensitivity condom. The web contains at least one of a spermicide, an anti-bacterial agent, and an anti-viral agent.

7 Claims, 1 Drawing Sheet

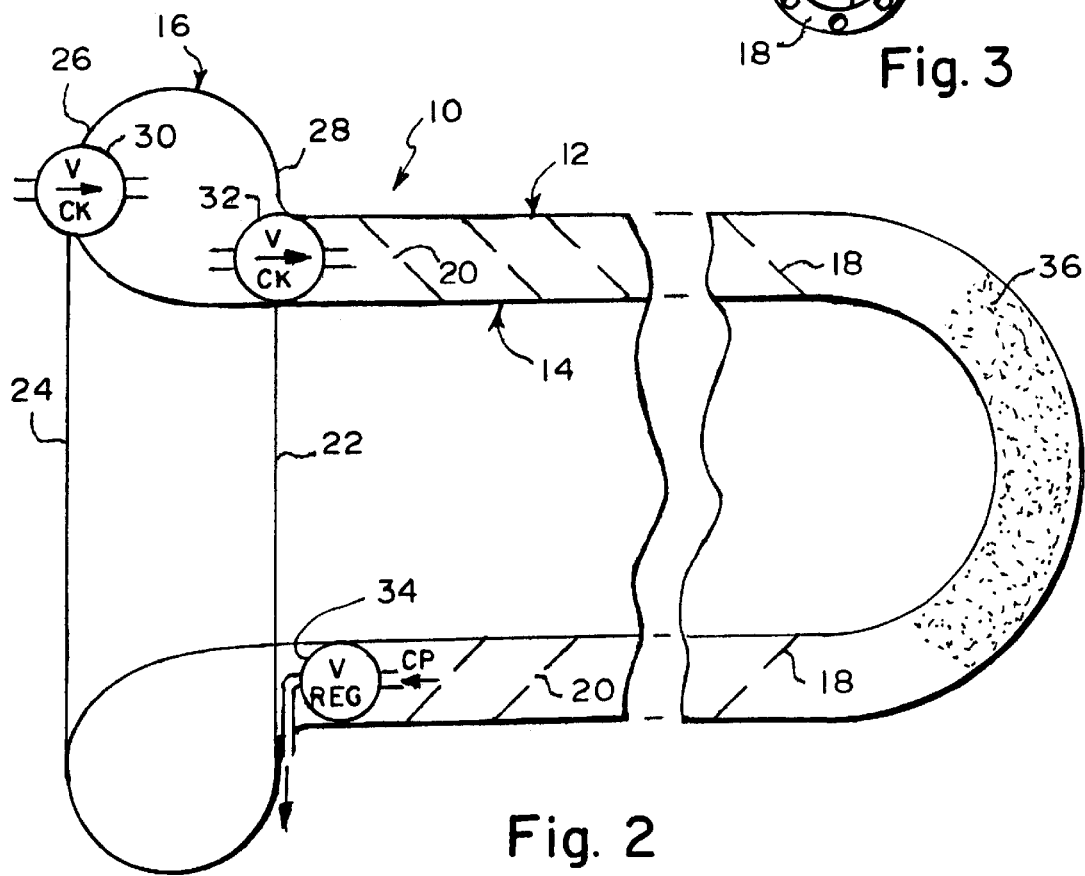

INCREASED SENSITIVITY CONDOM FOR SIMULTANEOUSLY REDUCING THE TRANSMISSION OF SEXUALLY TRANSMITTED DISEASES

CROSS REFERENCE TO RELATED APPLICATIONS

The instant application is a nonprovisional application of U.S. provisional application No. 60/407,728, filed on Sep. 3, 2002, and entitled EXTENDED PLEASURE CONDOM, and it is respectfully requested that this application be accorded the benefit under 35 USC 119(e) of said U.S. provisional application.

BACKGROUND OF THE INVENTION

1. Field of the Invention

The present invention relates to a condom. More particularly, the present invention relates to an increased sensitivity condom for simultaneously reducing the transmission of sexually transmitted diseases.

2. Description of the Prior Art

Numerous innovations for condoms have been provided in the prior art that will be described. Even though these innovations may be suitable for the specific individual purposes to which they address, however, they differ from the present invention.

A FIRST EXAMPLE, U.S. Pat. No. 4,281,648 to Rogers teaches an inflatable condom, prophylactic or prosthetic device having a conventional anterior portion and retaining ring or reinforced edge with an expandable secondary portion extending from the anterior member, and having an air duct extending inside the anterior portion in communication with the secondary portion to facilitate controlled inflation of the secondary portion responsive to manipulation of a pressure bulb.

A SECOND EXAMPLE, U.S. Pat. No. 4,432,357 to Rogers teaches a condom having a plurality of deformable sealed chambers along at least a portion of the length thereof, rheopexic fluid being filled in the deformable sealed chambers. When the chambers are deformed during use of the condom, shear stress is applied to the rheopexic fluid due to deformation of the sealed chambers to cause the rheopexic fluid to increase its consistency as a function of increasing shear stress applied thereto, thereby providing a stiffening effect to the condom.

A THIRD EXAMPLE, U.S. Pat. No. 5,331,974 to Sook teaches a multi-purpose sexual device usable as a condom usage comprising an insertion part, a pressure part and an air hole with two plys of outer and inner sheets sealed in conformance with its sealing line forming air spaces between the outer and inner sheets of insertion part and pressure part by filling with the proper amount of air blown in through the air hole.

A FOURTH EXAMPLE, U.S. Pat. No. 5,377,692 to Pfeil teaches a vibrating condom or device having an inflatable vibrating region or a self-activated vibrating region which contacts the clitoris or vaginal walls. The inflation of such vibrating region is achieved by the transport of air or fluid from a power unit while the self-activated, vibrating region could be achieved by an external or imbedded power source.

A FIFTH EXAMPLE, U.S. Pat. No. 5,622,186 to Schwartz teaches prophylactic devices and methods for assisting in establishing and maintaining male erectile function. Open ended elastic sheaths with portions having different elasticity than have other portions, which portions of different elasticity cause selective constriction around and/or along selected portions of the penis by differential external pressures applied to said selected portions so as to not impede arterial blood flow to the penis but impede venous blood flow from the penis and thereby establish and maintain the penis in an erectile position. Various sheath configurations for the purpose include portions with lesser radius laterally of the longitudinal center axis of the sheath, or with more rigid portions, or with thicker portions, or with a balloon-like internal chamber fillable with a liquid or gas.

A SIXTH EXAMPLE, U.S. Pat. No. 5,623,945 to Shecterle et al. teaches a two layer prophylactic device taking the form of a male or female condom or female diaphragm. The invention includes two latex layers bonded to one another along a spiral path which defines a corresponding spiral chamber between the latex layers. This spiral chamber extends between two compliant chambers at opposed ends of the device and is filled with a pharmacological fluid to help kill disease-bearing microbes and sperm cells which may permeate through the device during coitus. Due to the unique spiral chamber design leading between the complaint chambers, this pharmacological fluid remains uniformly dispersed during coitus and the device is less subject to rupture. Should one layer rupture during use, the pharmacological fluid will flow through the rupture and coat the adjacent sex organ. The present invention is specially effective in preventing unwanted pregnancies and the transmission of sexually transmitted diseases.

It is apparent that numerous innovations for condoms have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide an increased sensitivity condom for reducing the transmission of diseases that avoids the disadvantages of the prior art.

ANOTHER OBJECT of the present invention is to provide an increased sensitivity condom for reducing the transmission of diseases that is simple to use.

BRIEFLY STATED, STILL ANOTHER OBJECT of the present invention is to provide an increased sensitivity condom for reducing the transmission of diseases. A penis-facing inner sheath extends in a vagina-facing outer sheath, and together therewith, cooperate with a ring. The penis-facing inner sheath is attached to the vagina-facing outer sheath by a web that has apertures therein extending between the penis-facing inner sheath and the vagina-facing outer sheath. The ring is a pump that upon a thrust compresses and draws air in from the ambient through a first check valve in a male-facing side of the ring, out a second check valve in a female-facing side of the ring, and through the apertures in the web to inflate the increased sensitivity condom for reducing the transmission of diseases, while the relief valve prevents rupturing of the increased sensitivity condom for reducing the transmission of diseases. The web contains at least one of a spermicide, an anti-bacterial agent, and an anti-viral agent.

The novel features which are considered characteristic of the present invention are set forth in the appended claims. The invention itself, however, both as to its construction and its method of operation, together with additional objects and advantages thereof, will be best understood from the fol-

DESCRIPTION OF THE DRAWING

The figures of the drawing are briefly described as follows:

FIG. 1 is a diagrammatic side elevational view, partially in section, of the present invention;

FIG. 2 is an enlarged diagrammatic cross sectional view, with parts broken away, taken along line 2—2 in FIG. 1; and FIG. 3 is a diagrammatic cross sectional view taken along line 3—3 in FIG. 1.

LIST OF REFERENCE NUMERALS UTILIZED IN THE DRAWING 10 increased sensitivity condom for reducing the transmission of diseases of present invention
12 vagina-facing outer sheath
14 penis-facing inner sheath
16 ring
18 plurality of webs
20 apertures in plurality of webs 18
22 open end of penis-facing inner sheath 14
24 open end of vagina-facing outer sheath 12
26 ambient-facing input side of ring 16
28 output side of ring 16
30 first check valve of ambient-facing input side 26 of ring 16 for receiving air from ambient
32 second check valve of output side 28 of ring 16
34 relief valve of vagina-facing outer sheath 12
36 filling between plurality of webs 18

DESCRIPTION OF THE PREFERRED EMBODIMENT

Referring now to the figures, in which like numerals indicate like parts, and particularly to FIG. 1, the increased sensitivity condom for reducing the transmission of diseases of the present invention is shown generally at 10.

The configuration of the increased sensitivity condom for reducing the transmission of diseases 10 can best be seen in FIGS. 2 and 3, and as such, will be discussed with reference thereto.

The increased sensitivity condom for reducing the transmission of diseases 10 comprises a vagina-facing outer sheath 12, a penis-facing inner sheath 14, and a ring 16. The penis-facing inner sheath 14 extends in the vagina-facing outer sheath 12, and together therewith, cooperate with the ring 16.

The penis-facing inner sheath 14 is attached to the vagina-facing outer sheath 12 by a plurality of webs 18. Each web 18 has apertures 20 therein that extend between the penis-facing inner sheath 14 and the vagina-facing outer sheath 12.

The penis-facing inner sheath 14 has an open end 22, the vagina-facing outer sheath 12 has an open end 24, and the ring 16 has a male-facing input side 26 and a female-facing output side 28.

The open end 22 of the penis-facing inner sheath 14 is attached to the female-facing output side 28 of the ring 16 and the open end 24 of the vagina-facing outer sheath 12 is attached to the male-facing input side 26 of the ring 16.

The male-facing input side 26 of the ring 16 has a first check valve 30, the female-facing output side 28 of the ring 16 has a second check valve 32, and the vagina-facing outer sheath 12 has a relief valve 34 in proximity to the ring 16.

The ring 16 is a pump that upon a thrust compresses and draws air in through the first check valve 30 from the ambient, out the second check valve 32, and through the apertures 20 in the plurality of webs 18 to inflate the increased sensitivity condom for reducing the transmission of diseases 10. The relief valve 34 prevents rupturing of the increased sensitivity condom for reducing the transmission of diseases 10.

The plurality webs 18 has a filling 36 therebetween that is at least one of a spermicide, an anti-bacterial agent, and an anti-viral agent.

It will be understood that each of the elements described above, or two or more together, may also find a useful application in other types of constructions differing from the types described above.

While the invention has been illustrated and described as embodied in an increased sensitivity condom for reducing the transmission of diseases, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An increased sensitivity condom for reducing the transmission of diseases, comprising:
    a) a) vagina-facing outer sheath;
    b) a) penis-facing inner sheath; and
    c) a) ring;
    wherein said penis-facing inner sheath extends in said vagina-facing outer sheath, and together therewith, cooperate with said ring, wherein said penis-facing inner sheath is attached to said vagina-facing outer sheath by a plurality webs, wherein said plurality of webs have apertures therein; and
    wherein said apertures in said web extend between said penis-facing inner sheath and said vagina-facing outer sheath, wherein said penis-facing inner sheath has an open end, wherein said vagina-facing outer sheath has an open end, wherein said ring has:
        i) a male-facing input side; and
        ii) a female-facing output side, wherein said male-facing input side of said ring has a first check valve.

2. The condom as defined in claim 1, wherein said open end of said penis-facing inner sheath is attached to said female-facing output side of said ring.

3. The condom as defined in claim 1, wherein said open end of said vagina-facing outer sheath is attached to said male-facing input side of said ring.

4. The condom as defined in claim 1, wherein said female-facing output side of said ring has a second check valve.

5. The condom as defined in claim 4 wherein said vagina-facing outer sheath has a relief valve in proximity to said ring.

6. The condom as defined in claim 5, wherein said ring is a pump;
    wherein said pump upon a thrust compresses and draws air in through said first check valve from the ambient, out said second check valve, and through said apertures in said plurality of webs to inflate said increased sensitivity condom for reducing the transmission of diseases; and wherein said relief valve prevents rupturing of said increased sensitivity condom for reducing the transmission of diseases.

7. The condom as defined in claim 1, wherein said plurality of webs have a filling therebetween; and wherein said filling is at least one of a spermicide, an anti-bacterial agent, and an anti-viral agent.

* * * * *